(12) United States Patent
Kojima

(10) Patent No.: US 10,633,634 B2
(45) Date of Patent: Apr. 28, 2020

(54) METHOD FOR PREPARING BONE MARROW CELL AGGREGATE

(71) Applicant: PUBLIC UNIVERSITY CORPORATION YOKOHAMA CITY UNIVERSITY, Yokohama-shi, Kanagawa (JP)

(72) Inventor: Nobuhiko Kojima, Yokohama (JP)

(73) Assignee: PUBLIC UNIVERSITY CORPORATION YOKOHAMA CITY UNIVERSITY, Yokohama-Shi (JP)

( * ) Notice: Subject to any disclaimer, the term of this patent is extended or adjusted under 35 U.S.C. 154(b) by 0 days.

(21) Appl. No.: 15/661,654

(22) Filed: Jul. 27, 2017

(65) Prior Publication Data
US 2017/0321191 A1  Nov. 9, 2017

Related U.S. Application Data

(63) Continuation-in-part of application No. PCT/JP2016/051009, filed on Jan. 14, 2016.

(30) Foreign Application Priority Data

Jan. 28, 2015  (JP) ................................. 2015-014194

(51) Int. Cl.
*C12N 5/077* (2010.01)
*C12N 5/00* (2006.01)
(Continued)

(52) U.S. Cl.
CPC ............ *C12N 5/0669* (2013.01); *C12N 5/00* (2013.01); *A61L 27/00* (2013.01); *C12M 3/00* (2013.01);
(Continued)

(58) Field of Classification Search
None
See application file for complete search history.

(56) References Cited

U.S. PATENT DOCUMENTS

2008/0241870 A1  10/2008  Kale et al.
2010/0152491 A1   6/2010  Sirigireddy
2014/0235481 A1   8/2014  Steward et al.

FOREIGN PATENT DOCUMENTS

JP      2008-531166 A      8/2008
WO   WO 2004/104166 A1   12/2004

OTHER PUBLICATIONS

Kubota et al., Cancer Res. 41: 3052-3057 (1981).*
(Continued)

*Primary Examiner* — Erin M. Bowers
(74) *Attorney, Agent, or Firm* — Birch, Stewart, Kolasch & Birch, LLP

(57) ABSTRACT

The present invention provides a technique which enables organization of bone marrow cells by a simple method in a short period of time.
A method for preparing a bone marrow cell aggregate, comprising adding a liquid containing a bone marrow cell population to a medium containing a swellable material and culturing the bone marrow cell population in the presence of the swellable material. A method for reassembling a bone marrow tissue, comprising adding a liquid containing a bone marrow cell population to a medium containing a swellable material and culturing the bone marrow cell population in the presence of the swellable material.
According to common knowledge in the art, it has been considered difficult to reorganize once disintegrated bone marrow tissue without changing the cell composition (that is, without adding any adherent cell or extracellular matrix which will work as a "connecting material (binder)"). Indeed, it was impossible to aggregate bone marrow cells by
(Continued)

Examination of Methods for Assembling Bone Marrow-Like Tissue

U-bottom
96-well plate

Hanging drop
method

Methylcellulose
medium

After three days of culture        After one day of culture conventional methods. As a result of its achievement, the present invention changes such conventional thought and results and provides a major breakthrough technique pertaining to 3D culture of bone marrow cells. It has also been confirmed that culture of a bone marrow-like tissue reassembled by the method of the present could be continued up to day 14 in the MC medium.

15 Claims, 2 Drawing Sheets

(51) Int. Cl.
    *A61L 27/00*     (2006.01)
    *C12M 3/00*     (2006.01)

(52) U.S. Cl.
    CPC ...... *C12N 2513/00* (2013.01); *C12N 2533/70* (2013.01); *C12N 2533/78* (2013.01); *C12N 2539/00* (2013.01)

(56) References Cited

OTHER PUBLICATIONS

Suda, Kotsuzui Saibo no Baiyoho, Soshiki Bai yo no Gijutsu Oyo Hen, 3rd Edition, 2nd print, Tokyo: Asakura Publishing Co., Ltd., Sep. 10, 1997.*
Extended European Search Report dated Jul. 6, 2018, in European Patent Application No. 16743116.2.
Gupta et al., "Human CD34+ Bone Marrow Cells Regulate Stromal Production of Interleukin-6 and Granulocyte Colony-Stimulating Factor and Increase the Colony-Stimulating Activity of Stroma," Blood (May 16, 1988), vol. 91, No. 10, pp. 3724-3733.
Bianchi Scarra et al., "Composition of Human Granulocytic Colonies as a Function of the Purification Stage of CSF", Scand J Haematol, vol. 23, 1979, pp. 329-338.
Dao et al., "Normal Human Bone Marrow Cultures in Vitro: Cellular Composition and Maturation of the Granulocytic Colonies", British Journal of Haematology, vol. 37, 1977, pp. 127-136.
International Search Report (PCT/ISA/210) issued in PCT/JP2016/051009, dated Mar. 22, 2016.
Kojima et al., "Rapid aggregation of heterogeneous cells and multiple-sized microspheres in methylcellulose medium", Biomaterials, vol. 33, 2012, pp. 4508-4514.
Sayo et al., "Rapid formation of the bone marrow-like tissue", Biofabrication 2015, F3.3. [online], Nov. 8, 2015, Internet: <http://biofabrication2015.org/preliminaryprogram/>, 8 pages.
Written Opinion (PCT/ISA/237) issued in PCT/JP2016/051009, dated Mar. 22, 2016.
English translation of International Preliminary Report on Patentability dated Aug. 3, 2017, in PCT International Application No. PCT/JP2016/051009.
English language translation of SAYO et al., "Bunsan Jotai no Kotsuzui Saibo o Mochiita 3 Jigentekina Kotsuzuiyo Soshiki no Sakusei", Dai 38 Kai the Molecular Biology Society of Japan, Dai 88 Kai the Japanese Biochemical Society Taikai Godo Taikai, 2P1049, Nov. 16, 2015, 1 page.
English language translation of SAYO et al., "in vitro ni Okeru Kotsuzuiyo Soshiki no Sakusei", The Japanese Society for Regenerative Medicine Zasshi, vol. 14, Feb. 1, 2015, p. 193.
English language translation of SUDA, Toshio, edited by the Japanese Tissue Culture Association, Kotsuzui Saibo no Baiyoho, Soshiki Bai yo no Gijutsu Oyo Hen, 3rd edition, 2nd print, Tokyo: Asakura Publishing Co., Ltd., Sep. 10, 1997, pp. 297-300.

* cited by examiner

Examination of Methods for Assembling Bone Marrow-Like Tissue

Comparison between Bone Marrow Tissue and Reassembled Bone Marrow-Like Tissue

Engraftment of Mesenchymal Cells

METHOD FOR PREPARING BONE MARROW CELL AGGREGATE

This application is a Continuation-in-Part of PCT International Application No. PCT/JP2016/051009, filed on Jan. 14, 2016, which claims priority under 35 U.S.C. 119(a) to patent application Ser. No. 2015-014194, filed in Japan on Jan. 28, 2015, all of which are hereby expressly incorporated by reference into the present application.

TECHNICAL FIELD

The present invention relates to a method for preparing a bone marrow cell aggregate. More specifically, the present invention relates to a method for organizing bone marrow cells by three-dimensional (3D) culture.

BACKGROUND ART

Bone marrow tissue in animals such as human or mouse plays an important role as a hematopoietic tissue. A technique for reassembling bone marrow tissue is very important for elucidation of the mechanisms of hematopoiesis and diseases associated therewith. However, since bone marrow is mostly composed of hemocytes, it has been difficult to reorganize once disintegrated.

As a culture technique pertaining to bone marrow, Dexter culture is known (Non-Patent Document No. 1: Dexter T M, Allen T D, Lajtha L G. Conditions controlling the proliferation of haemopoietic stem cells in vitro. J Cell Physiol. 1977 June; 91(3):335-44). This is a culture method which uses stroma cells as a feeder and enables hematopoietic stem cells to be maintained thereon or differentiated into various cells. This culture is performed in planar environments.

A technique is also known in which the above-described culture is performed with 3D scaffolds (Non-Patent Document No. 2: Nichols J E, Cortiella J, Lee J, Niles J A, Cuddihy M, Wang S, Bielitzki J, Cantu A, Mlcak R, Valdivia E, Yancy R, McClure M L, Kotov N A. In vitro analog of human bone marrow from 3D scaffolds with biomimetic inverted colloidal crystal geometry. Biomaterials. 2009 February; 30(6):1071-9; Non-Patent Document No. 3: Leisten I, Kramann R, Ventura Ferreira M S, Bovi M, Neuss S, Ziegler P, Wagner W, Knüchel R, Schneider R K. 3D co-culture of hematopoietic stem and progenitor cells and mesenchymal stem cells in collagen scaffolds as a model of the hematopoietic niche. Biomaterials. 2012 February; 33(6):1736-47).

Yu-usuke Torisawa et al. of the Wyss Institute, Harvard University have reported a research into a technique using a micro-fluid device for 3D reassembly of bone marrow (Non-Patent Document No. 4: Yu-suke Torisawa, Catherine S Spina, Tadanori Mammoto, Akiko Mammoto, James C Weaver, Tracy Tat, James J Collins, Donald E Ingber, Bone marrow-on-a-chip replicates hematopoietic niche physiology in vitro, Nature Methods, Vol 11, JUNE, 663-669 2014). They report that various hematopoietic events can be confirmed in vitro. A procedure for actual reassembling consists of filling the hollow part of cylindrical poly(dimethylsiloxane) (PDMS) with materials which reassemble bone and embedding the PDMS in the body of a mouse to thereby reassemble bone marrow together with bone. When the device is embedded in the mouse body, no living cells are used at all and bone marrow cells migrate by way of blood. Transplantation requires a period of 8 weeks. After 8 weeks, bone marrow tissue organized in the body is taken out, followed by perfusion in vitro using the micro-fluid device. Thus, hematopoietic events are investigated.

PRIOR ART LITERATURE

Non-Patent Documents

Non-Patent Document No. 1: Dexter T M, Allen T D, Lajtha L G. Conditions controlling the proliferation of haemopoietic stem cells in vitro. J Cell Physiol. 1977 June; 91(3):335-44.

Non-Patent Document No. 2: Nichols J E, Cortiella J, Lee J, Niles J A, Cuddihy M, Wang S, Bielitzki J, Cantu A, Mlcak R, Valdivia E, Yancy R, McClure M L, Kotov N A. In vitro analog of human bone marrow from 3D scaffolds with biomimetic inverted colloidal crystal geometry. Biomaterials. 2009 February; 30(6):1071-9

Non-Patent Document No. 3: Leisten I, Kramann R, Ventura Ferreira M S, Bovi M, Neuss S, Ziegler P, Wagner W, Knüchel R, Schneider R K. 3D co-culture of hematopoietic stem and progenitor cells and mesenchymal stem cells in collagen scaffolds as a model of the hematopoietic niche. Biomaterials. 2012 February; 33(6):1736-47

Non-Patent Document No. 4: Yu-suke Torisawa, Catherine S Spina, Tadanori Mammoto, Akiko Mammoto, James C Weaver, Tracy Tat, James J Collins, Donald E Ingber, Bone marrow-on-a-chip replicates hematopoietic niche physiology in vitro, Nature Methods, Vol 11, JUNE, 663-669 2014

DISCLOSURE OF THE INVENTION

Problem for Solution by the Invention

Conventional methods have a problem that the culture system consists of stroma cells and hematopoietic stem cells. It is believed that hematopoiesis occurring in actual bone marrow also involves cells other than stroma cells and 3D positional relations would also be important. In view of these points, Dexter culture or 3D culture thereof is not considered to reflect all the functions of bone marrow.

Although the approach of Dr. Torisawa et al. enables assays of various types of hematopoiesis in 3D environments, the device need be embedded in a mouse body for 8 weeks in order to organize bone marrow. Accordingly, this approach would not be appropriate for the purpose of, e.g., examining the properties of the bone marrow of patients in hospital. In addition, unexpected elements might be involved in the mouse body to potentially affect the bone marrow tissue.

It is an object of the present invention to provide a technique which enables organization of bone marrow cells by a simple method in a short period of time.

Means to Solve the Problem

By employing a cell aggregation method using a—liquid culture medium containing a swellable material, the present inventor successfully organized bone marrow cells from a disintegrated state in a short period of time (about 24 hours). This has led to the accomplishment of the present invention. Briefly, the present invention provides a method for preparing a bone marrow cell aggregate, comprising adding a liquid containing a bone marrow cell population to a medium containing a swellable material and culturing the bone marrow cell population in the presence of the swellable material. The present invention also provides a method for reassembling a bone marrow tissue, comprising adding a liquid containing a bone marrow cell population to a medium containing a swellable material and culturing the bone marrow cell population in the presence of the swellable material.

According to the present invention, it is possible to prepare a tissue comprising not only blood cells but also vascular endothelial cells and mesenchymal cells. Potentially, the present invention is capable of reassembling a hematopoietic niche. Further, it is expected that the present invention is applicable to preparation of various disease models and evaluation of the functions and properties of various cells that constitute bone marrow.

Effect of the Invention

According to the present invention, it has become possible to prepare a bone marrow cell aggregate comprising bone marrow cells by a simple method in a short period of time. The method of the present invention also enables reassembly of a bone marrow tissue.

The present specification encompasses the contents disclosed in the specification and/or the drawings of Japanese Patent Application No. 2015-14194 based on which the present application claims priority.

BEST MODES FOR CARRYING OUT THE INVENTION

Figure 1:
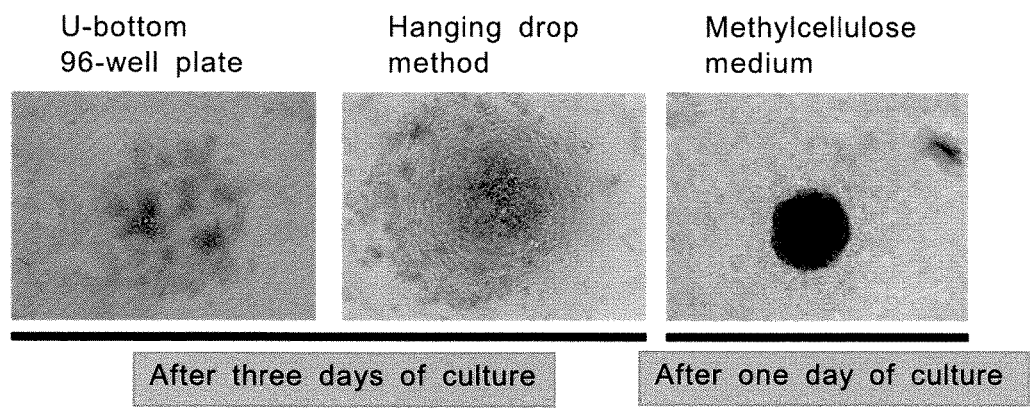
FIG. 1. Conventional aggregation methods such as a method using U-bottom 96-well plate or the hanging-drop method were unable to aggregate disintegrated bone marrow cells even after three days of culture. On the other hand, when a medium was used that had methylcellulose dispersed therein as a swellable material, an aggregated state could be generated in about 10 minutes and by culturing the resultant cells for subsequent 24 hours, a tissue was obtained which did not disintegrate even when it was taken out of the methylcellulose medium.

Hereinbelow, the present invention will be described in more detail.

The present invention provides a method for preparing a bone marrow cell aggregate, comprising adding a liquid containing a bone marrow cell population to a medium containing a swellable material and culturing the bone marrow cell population in the presence of the swellable material.

The swellable material may be any material that tends to swell upon absorption of a liquid such as water. Specific examples of swellable materials include, but are not limited to, polymers such as methylcellulose, pectin or carboxymethylcellulose.

As the medium, DMEM, αMEM or any other type of conventional medium may be used.

The term "bone marrow cell" refers to those cells that constitute bone marrow. This term encompasses the so-called hemocytes (parenchymal cells) such as differentiated leukocytes and erythrocytes, progenitor cells thereof and hematopoietic stem cells, as well as vascular endothelial cells, adipocytes, reticular cells, adventitial reticular cells, endosteal cells, osteoblasts and the like which constitute hematopoietic niche.

The term "bone marrow cell population" refers to a population consisting of two or more cells comprising at least one bone marrow cell. Specific examples of the bone marrow cell population include, but are not limited to, a mixture of bone marrow cells obtained by syringing bone marrow tissue taken from a living body; the above-mentioned bone marrow cell mixture to/from which a specific cell (e.g., a rare cell among those cells that constitute bone marrow) is added/removed; the above-mentioned bone marrow cell mixture to which a genetically engineered cell is added; ES cells or iPS cells per se; and various progenitor or mature cells differentiated therefrom. Further, when an extramedullary hematopoiesis model is intended, those cells that constitute spleen or kidney may be given as examples. Further, it may be worthwhile to add other cells to the population, and it might be possible to prepare a disease (pyogenic osteomyelitis) model by adding bacteria to the population.

The liquid to contain bone marrow cell populations may be exemplified by, but not limited to, DMEM and the like.

Culture of bone marrow cell populations may be performed under such conditions that bone marrow cell populations are compulsorily maintained in an aggregated state in the presence of a swellable material.

Factors that affect the degree of aggregation of bone marrow cells may include, but are not limited to, the type, physical properties (molecular weight, etc.) and concentration of the swellable material used, as well as the cell count of the bone marrow cell population. When culture is to be performed by infusing a liquid containing a bone marrow cell population into a medium containing a swellable material, the volume of the liquid, and the method of its infusion, and the shape of liquid drops after infusion may also be factors which would affect the degree of aggregation.

When methylcellulose is used as a swellable material, the methylcellulose concentration in the medium may be 1-3% by mass. The higher the methylcellulose concentration, the faster the aggregation speed and the greater the driving force for aggregation. However, if the concentration is higher than 3% by mass, it then becomes difficult to disperse methylcellulose in the medium and the viscosity of the medium is so high that it becomes very difficult to handle. The cell count of a bone marrow cell population may be from about 100 to 100,000 per µl of a medium containing 1-3% by mass of methylcellulose. A bone marrow cell suspension (infusion) prepared to give a cell density of $1 \times 10^6$-$1 \times 10^8$ cells/ml, preferably $2 \times 10^7$ cells/ml, may be injected into methylcellulose-containing DMEM with a micropipette in 0.1-10 µl, preferably 1 µl, portions at appropriate intervals. The volume of methylcellulose-containing DMEM is determined appropriately depending on the culture vessel. A volume substantially equal to the volume of the medium that is to be added in conventional culture may be considered appropriate. An excess of the methylcellulose-containing DMEM will cause no problem except that it takes time to be degraded with an enzyme. A shortage of the methylcellulose-containing DMEM will cause several troubles such as a further increase in viscosity due to evaporation of water or the aggregate touching the bottom of culture equipment. If the droplets of the infusion injected into the medium assume a spherical shape, it is highly likely that the aggregate formed also assumes a spherical shape. The injected bone marrow cells become aggregated in about 10 minutes. The resultant cells are cultured as such in the methylcellulose-containing medium in a $CO_2$ incubator at 33-37° C. for 24 hours to 7 days until a bone marrow cell aggregate is obtained. These culture conditions may be appropriately changed. Bone marrow cell aggregates (3D tissues) in sizes of about 10 μm to about 1 mm can be prepared by the method of the present invention. For example, a bone marrow cell aggregate in a size of about 10 μm can be prepared from 0.1 μL of a bone marrow cell suspension at a cell density of $1 \times 10^6$ cells/ml. A bone marrow cell aggregate in a size of about 1 mm can be prepared from 10 μL of a bone marrow cell suspension at a cell density of $1 \times 10^8$ cells/ml. For collecting the resultant bone marrow cell aggregate, the viscosity of the methylcellulose-containing medium may be reduced by degrading methylcellulose with cellulase since said medium would otherwise have such a high viscosity that collecting operations are difficult to perform. Even in the case of using a swellable material other than methylcellulose, treatments for reducing the viscosity of a swellable material-containing medium are preferably carried out (e.g., treatment with a degrading enzyme, change toward lower temperatures, slight pH change, etc.). Degrading enzymes that decompose cell-constituting components are cytotoxic and therefore undesirable. As regards methylcellulose, its skeleton (cellulose) is degraded with cellulase. Cellulose is a component of plant cells but absent from human cells. Cellulase would, therefore, have little toxicity.

According to the method of the present invention, a bone marrow aggregate containing bone marrow cells is obtained. The cell aggregate as used herein refers to a state in which individual cells bind together and it is a concept encompassing a 3D tissue (i.e., a plurality of cells gather three-dimensionally to adhere to each other), a spheroid, and an organoid.

According to the method of the present invention, it becomes possible to reassemble bone marrow tissue even if it has been once disintegrated. Therefore, the present invention also provides a method for reassembling a bone marrow tissue, comprising adding a liquid containing a bone marrow cell population to a medium containing a swellable material and culturing the bone marrow cell population in the presence of the swellable material.

In the present invention, even cells without adhesion capacity can be brought into an aggregated state where cells are in mutual contact, in about 10 minutes. In one embodiment of the present invention, aggregation is performed in a medium containing a swellable material (e.g., a medium having a polymer (methylcellulose) dispersed therein). The resultant aggregate is cultured as suspended with its periphery being surrounded by the swellable material. The aggregate immediately after becoming aggregated will be disintegrated again if taken out of the medium but upon continued culture for an additional period (say, 24 hours), the cells bind together to form a tissue. A niche can be reproduced even from rare cells by allowing them to contribute to the above-described process of organization.

In the present invention, even cells other than stroma cells can be rendered to contribute to 3D bone marrow tissue.

Further, by combining the present invention with cell isolation techniques, bone marrow constituting cells (especially rare cells) can be freely added or removed, making it possible to examine their effect on hematopoiesis. It is also possible to add a genetically engineered cell to examine its effect.

EXAMPLES

Hereinbelow, the present invention will be described in more detail with reference to the following Examples.

Example 1

Methods and Materials
Isolation of Bone Marrow Cells

C57BL/6NcrSlc male mice (8 week old) were anesthetized and euthanized by cervical spine fracture dislocation. Then, their legs were disinfected with 70% ethanol. An incision was made in the groin with scissors to peel off the skin and remove the muscles. The femur and the tibia were taken out. Either end of these bones was cut off. From one end, Dulbecco's Modified Eagle Medium (DMEM containing 10% fetal bovine serum and antibiotics) warmed to 37° C. was infused using a syringe with a 23G needle so that a bone marrow tissue was pushed out from inside of the bone. The thus collected bone marrow tissue was syringed to obtain a bone marrow cell suspension. The resultant suspension was transferred into a 15 ml centrifuge tube and centrifuged at 1000 rpm and 4° C. for three minutes. The supernatant was discarded. The cell pellet was loosened by tapping, followed by addition of 6 ml of a hypotonic solution. The resultant mixture was lightly pipetted and treated on ice for 10 minutes to thereby hemolyze erythrocytes. 6 ml of DMEM was added to the centrifuge tube. The cell suspension was lightly tapped. Then, the debris was removed with a 40 μm strainer to obtain bone marrow cells. This procedure is the conventional method for obtaining bone marrow cells, but depending on conditions of experiments, the present inventor skipped hemolysis and used bone marrow cells isolated together with erythrocytes.

Preparation of 3D Tissue (Aggregate) with Methylcellulose Medium

This preparation was performed based on the method previously reported by the inventor [1]. Methylcellulose (MC) (Sigma-Aldrich; Cat. No. M0512; Origin: hydroxyl group of cellulose was replaced by 27.5-31.5% by weight methoxy group; Viscosity: 3,500-5,600 cP; 2% in water (20° C.); Molecular weight: 88,000 (estimated value)) was dispersed in DMEM at a concentration of 3% to prepare an MC medium. A 2 ml aliquot of the medium was poured into a 35 mm Petri dish which was then left stationary for a while to remove bubbles and make the liquid surface flat. Subsequently, a bone marrow cell suspension prepared to give a cell density of $2 \times 10^7$ cells/ml was injected into the MC medium with a micropipette in 1 μl portions at appropriate intervals. The injected cells became aggregated in about 10 minutes. The cells were cultured as such in the MC medium for 1-7 days. For collecting the thus reassembled bone marrow tissue, the viscosity of the MC medium was reduced by degrading MC with cellulase because otherwise the medium would have such a high viscosity that collecting operations would be difficult to perform.

Preparation of 3D Tissue by Conventional Methods

As conventional methods for assembling a 3D tissue, a method using a U-bottom 96-well plate (with a low adhesion treated surface) and the hanging drop method were carried out. In the method using a 96-well plate, 5 μl of a bone marrow suspension prepared to give a cell density of $2 \times 10^7$ cells/ml was added to 100 μl of DMEM and cultured at 37° under 5% $CO^2$. In the hanging drop method, a cell suspension prepared to contain 20,000 bone marrow cells was poured in 20 μl portions onto the reverse side of the lid of a Petri dish. The lid was then placed over the Petri dish containing 15 ml of sterile water, followed by cell culture at 37° under 5% $CO_2$.

Hematoxylin-Eosin (HE) Staining and Immunostaining

After washing with phosphate-buffered saline (PBS), the aggregate was fixed with 4% paraformaldehyde at room temperature for 15 minutes. A small amount of 1% alginic acid solution containing about 10 aggregates was gelated by addition of 10% calcium chloride solution. The resultant gel was embedded in paraffin to prepare sections. Sliced samples were hydrophilized and then subjected to HE staining. Immunostaining was also performed using primary and secondary (fluorescence labeled) antibodies to CXCL12 and PDGFRα.

Results

Preparation of Aggregates with MC Medium and Reorganization of Bone Marrow Cells by Culture More than 98% of the cells that constitute bone marrow tissue are hemocytes that do not have a capacity to adhere to each other. Therefore, the conventional methods for three-dimensionally organizing a bone marrow tissue using adherent cells (i.e., the method using a U-bottom 96-well plate whose surface has been given cell non-adhesion treatment and the hanging drop method) are unable to yield 3D aggregates of bone marrow cells even after three days of culture (FIG. 1, left and middle). On the other hand, the method in which 1 μl of a cell suspension (containing approx. 20,000 bone marrow cells per μl) is injected into a MC medium is capable of compulsorily forming an aggregated state in a short period of time (10 minutes). If the cell population is taken out of the MC medium immediately after it is aggregated, the cells will as a matter of course return to a disintegrated state. However, by culturing the cells in the MC medium for at least 24 hours as they retain the aggregated state, it was possible to prepare a reassembled bone marrow tissue in which bone marrow cells adhered to each other even after they were taken out of the MC medium (FIG. 1, right). According to common knowledge in the art, it has been considered difficult to reorganize once disintegrated bone marrow tissue without changing the cell composition (that is, without adding any adherent cell or extracellular matrix which will work as a "connecting material (binder)"). Indeed, it was impossible to aggregate bone marrow cells by the conventional methods. As a result of its achievement, the present invention changes such conventional thought and results and provides a major breakthrough technique pertaining to 3D culture of bone marrow cells. It was also confirmed that culture of the bone marrow-like tissue reassembled by the method of the present invention could be continued up to day 14 in the MC medium.

Figure 2:
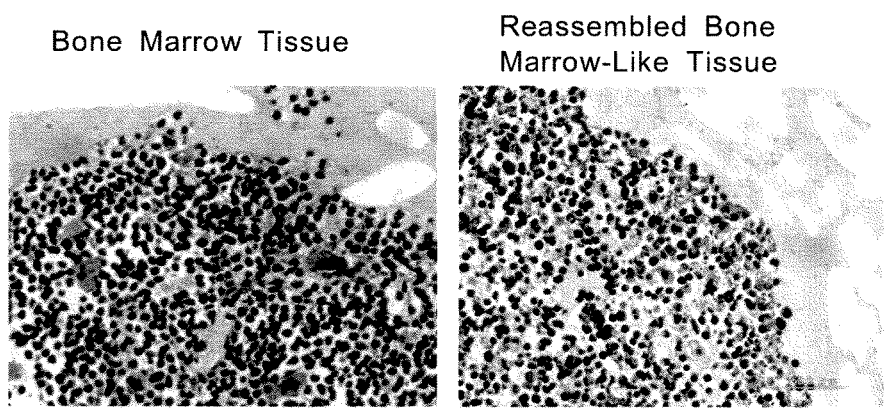
FIG. 2. The inside of the bone marrow tissue reassembled by 24 hours of culture (right panel) had a similar structure to normal bone marrow tissue (left panel), provided that the former had a somewhat lower cell density.

Comparison of Tissue Structures Between Actual Bone Marrow Tissue and Reassembled Bone Marrow Tissue An actual bone marrow tissue taken out of the femur and a bone marrow-like tissue reassembled in MC medium were compared for structure by preparing tissue sections. In the reassembled tissue, cell density was somewhat lowered because of dead cells, and vascular structures were found to have been eliminated. Although such differences were observed, the image of the reassembled tissue was relatively similar to the image of the actual bone marrow (FIG. 2).

Engraftment of Mesenchymal Cells

Figure 3:
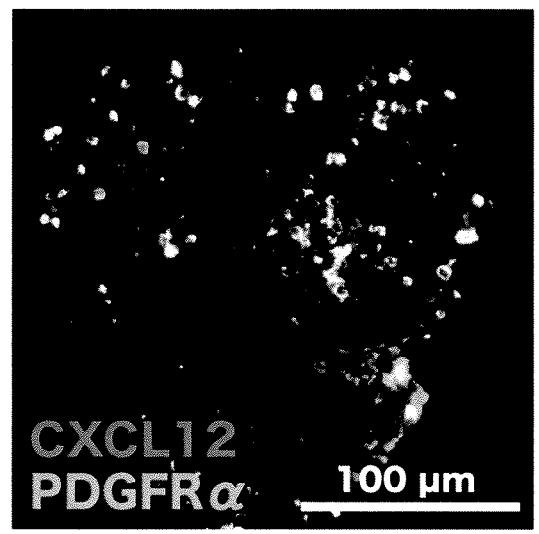
FIG. 3. The presence of mesenchymal cells expressing CXCL12 and PDGFRα could be confirmed in the reassembled bone marrow tissue.

It was examined whether or not CXCL12 positive cells (mesenchymal cell considered to be important for the constitution of hematopoietic niche) and PDGFRα positive cells (cells expressing the mesenchymal cell marker PDGFRα) were present inside of the reassembled bone marrow-like tissue. Briefly, paraffin sections of bone marrow-like tissue at Day 1 of culture were immuno-stained using antibodies to individual antigens. As a result, it was confirmed that these positive cells had been engrafted (FIG. 3). It was expected that by means of a further improvement on the culture method, the present invention would have the potential to contribute to such applications as examination of 3D hematopoietic niche structure.

Discussion

Now that bone marrow cells can be organized and cultured three-dimensionally by a simple method, it is expected that events that are specific to 3D environments and which have been impossible to obtain by conventional hematopoietic assays in 2D environments can be reproduced in vitro. It is also predicted that those experiments which have heretofore been difficult to carry out with human bone marrow or in animal experiments can be performed efficiently; for example, at the time of disintegration of bone marrow tissue, a specific cell alone is deleted or replaced with a genetically engineered cell and the subsequent behavior in 3D bone marrow-like tissue is observed. t The method of the present invention is therefore expected to become a technique useful in medical care and drug discovery.

REFERENCE

1. Kojima, N., Takeuchi, S. and Sakai, Y. Rapid aggregation of heterogeneous cells and multiple-sized microspheres in methylcellulose medium. Biomaterials, 33, 4508-4514 (2012)

Example 2

Preparation of 3D Tissue (Aggregate) with Pectin Medium

Figure 4:
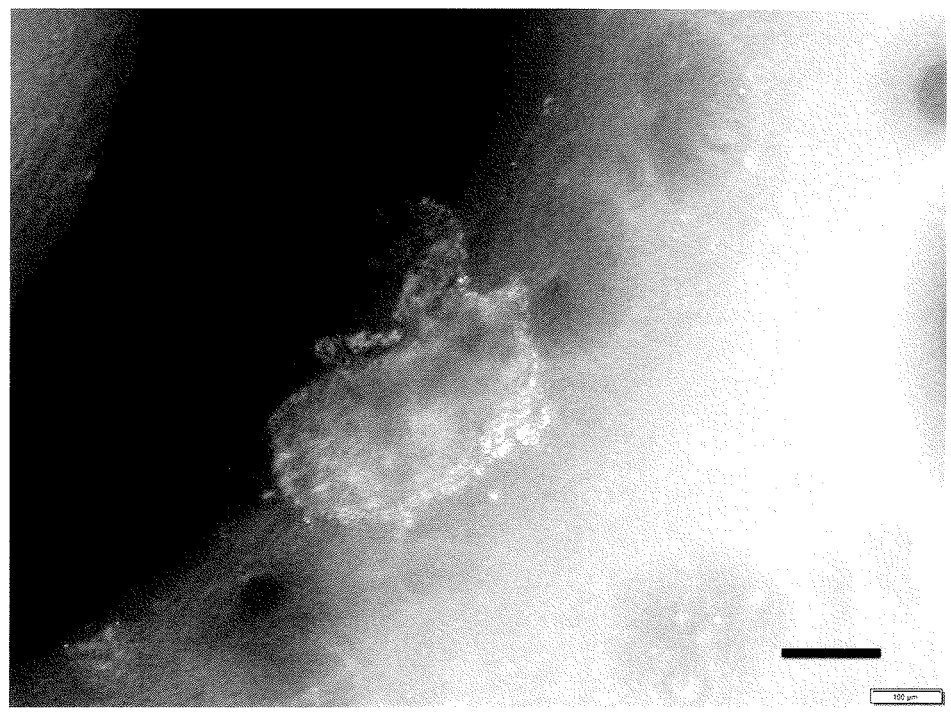
FIG. 4. The state of bone marrow cells 30 minutes after injection into a pectin medium. Scale bar is 200 µm.

In order to demonstrate that cell aggregation using a polymer other than methylcellulose is possible, pectin was used in this experiment. Briefly, pectin (Sigma-Aldrich; Cat. No. P9135-100G; derived from citrus peel) was dispersed in DMEM at a concentration of 6% to prepare a pectin medium. A 2 ml aliquot of the medium was poured into a 35 mm Petri dish which was then left stationary for a while to remove bubbles. Subsequently, a bone marrow cell suspension prepared to give a cell density of $2 \times 10^7$ cells/ml was injected into the pectin medium with a micropipette in 1 μl portions. The injected cells became aggregated in about 30 minutes which was longer than the time required when methylcellulose was used (FIG. 4). This would be due to the differences in molecular weight and concentration. Since pectin in solution yields acidity, it is anticipated that culture of cells in the pectin medium would not produce the same result as seen from culture in the methylcellulose medium; yet it was demonstrated that a polymer other than methylcellulose is also capable of aggregating bone marrow cells.

All publications, patents and patent applications cited herein are incorporated herein by reference in their entirety.

INDUSTRIAL APPLICABILITY

The present invention is applicable to preparation of bone marrow-associated disease models. With such models, it is possible to elucidate the mechanisms of diseases and to perform drug discovery screening.

The present invention is also applicable to bone marrow-associated regenerative medicine. For example, the present invention is applicable to reassembly of ectopic bone marrow tissue.

The invention claimed is:

1. A method for preparing a bone marrow cell aggregate, comprising:
   adding a liquid comprising a bone marrow cell population comprising blood cells and mesenchymal cells to a medium comprising a swellable material; wherein the swellable material comprises pectin or methylcellulose, wherein the liquid is added to the medium by infusion;
   culturing the bone marrow cell population in the medium in the presence of the swellable material until a bone marrow cell aggregate comprising blood cells and mesenchymal cells is formed; and
   removing the bone marrow cell aggregate from the medium, wherein cells of the bone marrow cell aggregate adhere to each other.

2. A method for reassembling a bone marrow tissue, comprising:
   adding a liquid comprising a bone marrow cell population comprising blood cells and mesenchymal cells to a medium comprising a swellable material; wherein the swellable material comprises pectin or methylcellulose, wherein the liquid is added to the medium by infusion;
   culturing the bone marrow cell population in the medium in the presence of the swellable material until a bone marrow tissue comprising blood cells and mesenchymal cells is reassembled; and
   removing the bone marrow tissue from the medium, wherein cells of the bone marrow tissue adhere to each other.

3. The method for reassembling a bone marrow tissue according to claim 2, wherein the tissue further comprises vascular endothelial cells.

4. The method according to claim 1 or 2, further comprising maintaining the formed or reassembled state in culture in the presence of the swellable material.

5. The method according to claim 1 or 2, wherein the swellable material is methylcellulose.

6. The method according to claim 1 or 2, wherein the methylcellulose concentration in the medium is 3% by mass.

7. The method according to claim 1 or 2, wherein the cell count of the bone marrow cell population is from 100 to 100,000 per μl of medium.

8. The method according to claim 1 or 2, wherein the bone marrow cell density of the liquid is $1\times10^6$ to $1\times10^8$ cells/ml.

9. The method according to claim 1 or 2, wherein the bone marrow cell density of the liquid is $2\times10^7$ cells/ml.

10. The method according to claim 1 or 2, wherein the volume of the liquid added is 0.1-10 μl.

11. The method according to claim 1 or 2, wherein the volume of the liquid added is 1 μl.

12. The method according to claim 1 or 2, wherein the bone marrow cell aggregate is formed, or the bone marrow tissue is reassembled, in about 10 minutes after adding the liquid to the medium comprising the swellable material.

13. The method according to claim 1 or 2, wherein the bone marrow cell population is cultured for at least 24 hours in MC medium.

14. The method according to claim 1 or 2, wherein the bone marrow cell population is cultured up to 14 days in MC medium.

15. The method according to claim 1 or 2, wherein the methylcellulose concentration in the medium is 1-3% by mass.

* * * * *